(12) United States Patent
Frank et al.

(10) Patent No.: US 8,380,285 B2
(45) Date of Patent: Feb. 19, 2013

(54) METHOD FOR CONTROLLING A MEASUREMENT OF A MAGNETIC RESONANCE DEVICE ON THE BASIS OF AN ELECTROCARDIOGRAM SIGNAL

(75) Inventors: Michael Frank, Erlangen (DE); Stefan Merkel, Erlangen (DE); Ernst Mustafa, Fürth (DE); Helmut Wrobel, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1469 days.

(21) Appl. No.: 12/001,444

(22) Filed: Dec. 11, 2007

(65) Prior Publication Data

US 2008/0139926 A1 Jun. 12, 2008

(30) Foreign Application Priority Data

Dec. 11, 2006 (DE) .................... 10 2006 058 332

(51) Int. Cl.
*A61B 5/05* (2006.01)
(52) U.S. Cl. ....................... 600/413; 600/521
(58) Field of Classification Search ............. 600/407, 600/410, 413
See application file for complete search history.

(56) References Cited

U.S. PATENT DOCUMENTS

| | | | |
|---|---|---|---|
| 3,552,386 A | 1/1971 | Horth | |
| 3,602,222 A | 8/1971 | Herndon | |
| 4,865,043 A * | 9/1989 | Shimoni | 600/513 |
| 5,503,159 A * | 4/1996 | Burton | 600/516 |
| 6,070,097 A * | 5/2000 | Kreger et al. | 600/521 |
| 2002/0151811 A1 | 10/2002 | Starobin et al. | |

FOREIGN PATENT DOCUMENTS

| | | |
|---|---|---|
| DE | 10 2005 027 438 A | 12/2006 |
| EP | 0429190 A2 | 5/1991 |
| WO | WO 99/04689 A1 | 2/1999 |

OTHER PUBLICATIONS

Friesen et al., "A Comparison of the Noise Sensitivity of Nine QRS Detection Algorithms", IEEE Transactions on Biomedical Engineering, Jan. 1990, pp. 85-98, vol. 37, No. 1.

* cited by examiner

*Primary Examiner* — Brian Casler
*Assistant Examiner* — Nasir S Shahrestani

(57) ABSTRACT

The method is related to control a measurement of a magnetic resonance device based on electrocardiogram signals of a patient detected by at least two channels. The method comprises the steps of: supplying the electrocardiogram signals in a first processing branch to a low pass filter and a derived value sum generator; comparing the output signal with a threshold value to generate a first comparison result; feeding the electrocardiogram signals in a second processing branch to a derived value generator; comparing said signals with an upper and a lower threshold value to generate a second comparison result; repeat the above steps for the second and if necessary further channels; evaluating all first and second comparison results for all channels in a weighted logic circuit; and triggering the measurement as a function of the result of the weighted logic circuit.

15 Claims, 3 Drawing Sheets

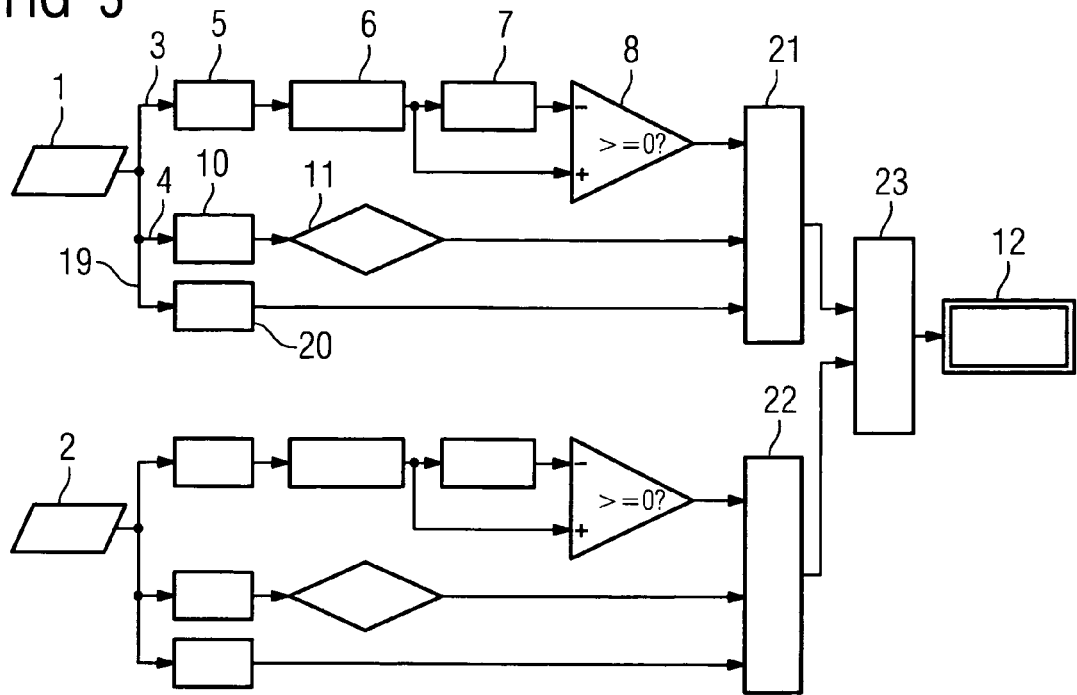
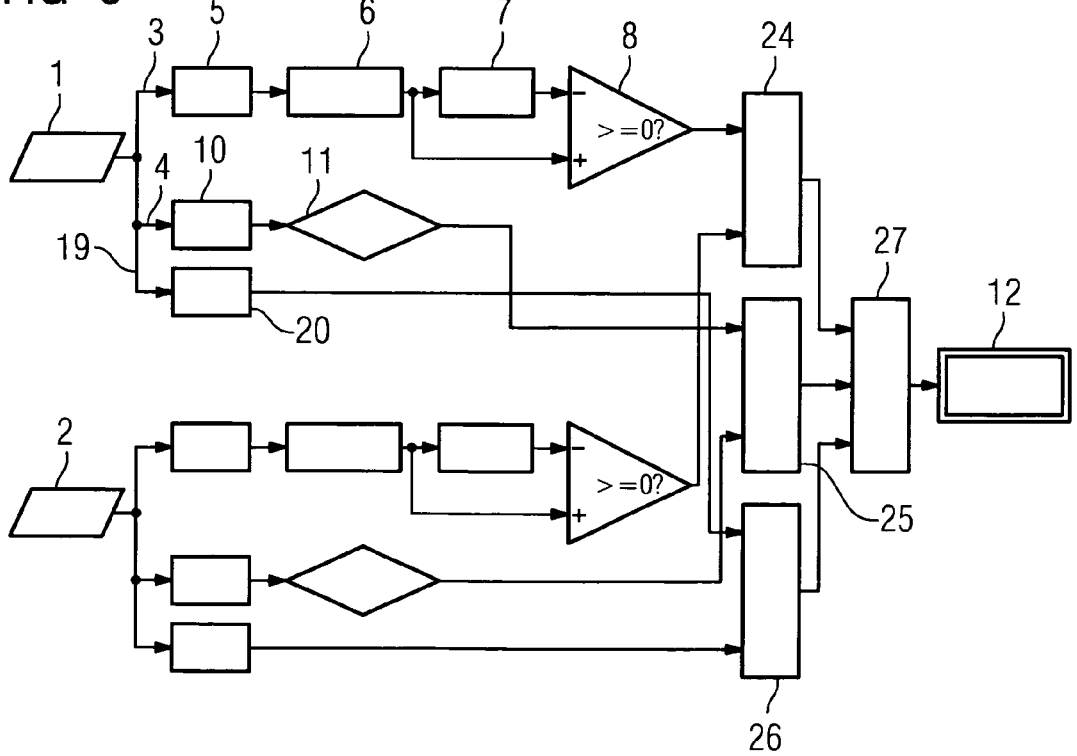

METHOD FOR CONTROLLING A MEASUREMENT OF A MAGNETIC RESONANCE DEVICE ON THE BASIS OF AN ELECTROCARDIOGRAM SIGNAL

CROSS REFERENCE TO RELATED APPLICATIONS

This application claims priority of German application No. 10 2006 058 332.9 filed Dec. 11, 2006, which is incorporated by reference herein in its entirety.

FIELD OF THE INVENTION

The invention relates to a method for controlling a measurement of a magnetic resonance device on the basis of an electrocardiogram signal (ECG signal).

BACKGROUND OF THE INVENTION

Magnetic resonance tomography (MR) requires the ECG signals of the patient to be detected in order to synchronize the triggering of the MR measurement sequences to the heartbeat of the patient. Similarly, the information relating to the current heart phase can be obtained by means of the ECG signal detected during an MR examination. If the ECG signals and the triggering and/or activation of the measurement sequence are not synchronized, there is a risk of the MR images containing movement artifacts.

In practice however, the detection of ECG signals is associated with difficulties, since the electrical and magnetic fields acting during the MR sequences couple into the ECG electronics system in a significantly interfering fashion, as a result of which the reliable determination of the heart phase is adversely affected. Besides these unwanted couplings into the ECG electronics system, the so-called magnetohydrodynamic effect occurs in the case of higher magnetic flux densities, which results in the T-wave of the heartbeat being overshot. The different phases of the heart cycle are designated in the field of electrocardiography with letters, by the sequence P-Q-R-S-T for instance. In this process, the R-wave shows the greatest amplitude, it constitutes the reference point of the triggering and must therefore be determined in a reliable fashion.

A method for the ECG triggering of a measurement sequence of a magnetic resonance device is known from U.S. Pat. No. 6,070,097, but the ECG signals of a patient are detected in this method via a single channel.

WO 99/04688 has proposed the detection of ECG signals via two channels, a vector display in a coordinate system is derived herefrom. The R-wave of the heart cycle is to be inferred from this display. It is however doubtful whether this method features adequate reliability, since this vector projection is dependent on many influences, it changes for instance if the patient holds his/her breath.

In the non pre-published application DE 10 2005 027 438 A1, a further improvement has been proposed in that the triggering of the measurement sequence is carried out if the ECG signal of at least one channel which is subjected to digital signal processing exceeds a threshold value and the derived value of the ECG signal or the sum of the derived values of the ECG signal lies within a defined interval in the case of both channels. The measurement sequence of the magnetic resonance device is then only triggered when a number of conditions are fulfilled at the same time.

SUMMARY OF THE INVENTION

The object underlying the invention is to specify a method which exhibits greater reliability for controlling a measurement of a magnetic resonance device on the basis of an electrocardiogram signal.

A method with the features of the claims is provided in order to achieve this object.

With the method according to the invention, ECG signals are detected via at least two channels. The ECG signals of the first channel are subjected to a signal processing, by feeding the ECG signals in a first processing branch to a lowpass filter and a derived value sum generator and by comparing the output signal with a threshold value supplied by a threshold value creator, so that a first comparison result is achieved. To this end, signal processing is carried out in a second processing branch in parallel, by the ECG signals in a second processing branch being fed to a derived value sum generator and being compared with an upper and a lower threshold value so that a second comparison result is achieved. These signal processing steps are repeated for the second channel and if necessary further channels which are present. All first and second comparison results are then evaluated for all channels in a weighted logic circuit, the measurement of the magnetic resonance device is consequently triggered as a function of the result of the weighted logic circuit.

A higher reliability in respect of the recognition of the R-wave is achieved with the method according to the invention, in particular, faulty activations through interferences which are generated by the gradient coils are avoided. The weighted logic circuit allows the influence of specific ECG signals to be amplified or restricted.

In accordance with a first variant of the method according to the invention, provision can be made in the method step f) for the MR measurement to be activated cyclically in each instance by means of a triggering at a trigger point in time, if necessary with a delay time set.

In accordance with a second variant of the method according to the invention, provision can be made in method step f) for the MR measurement to be started after an adjustable opening time and to be terminated after an adjustable closing time at a trigger point in time.

In accordance with a third variant of the method according to the invention, provision can be made in method step f) for the MR measurement to be carried out untriggered and for time stamps to be added to the detected MR measurement data as a function of the electrocardiogram signals, with the MR measurement data if necessary subsequently being correlated with the electrocardiogram signals and if necessary being interpolated.

With the method according to the invention, provision can be made for the derived value sum generator to form the sum of the first or second mathematical derived value of the ECG signals or a combination thereof.

Provision can also be made in accordance with the invention for the derived value generator to form the mathematical derivation or sum thereof.

In a further embodiment of the method according to the invention, provision can be made for the first and the associated second comparison result of a channel to be evaluated in a weighted logic circuit and for all results of the weighted logic circuits to be fed to a further weighted logic circuit, the measurement of the magnetic resonance device being triggered as a function of the result thereof. With this variant, all comparison results of a channel are thus fed in each instance to a weighted logic circuit, the results of the n logic circuits of the n channels are then fed to a further logic circuit arranged downstream thereof.

In accordance with an alternative embodiment of the invention, provision can be made for all first comparison results to be evaluated in a first weighted logic circuit and for all second comparison results to be evaluated in a second weighted logic circuit such that the result of the first and the second weighted logic circuit is fed to a further logic circuit, the measurement of the magnetic resonance device being triggered as a function of the result thereof. With this variant, all first comparison results are fed in each instance to a weighted logic circuit, similarly all second comparison results are also fed to another weighted logic circuit, the results of the two logic circuits are evaluated in a further logic circuit arranged downstream thereof.

According to a further variant of the method according to the invention, provision can be made for a signal processing to be carried out for at least one channel in a third and/or a further processing branch in addition to the two processing branches which have already been mentioned. A signal processing in the third and/or further processing branch can naturally also take place for all channels.

All third and if necessary further comparison results are preferably evaluated in a further weighted logic circuit and the result of all weighed logic circuits is fed to a further logic circuit, the measurement of the magnetic resonance device being triggered as a function of the result thereof.

In a further embodiment of the method according to the invention, provision can be made for the signal processing to include a method for pattern recognition and/or the application of fuzzy logic and/or a combination of filtering and threshold value formation.

With the method according to the invention, the used threshold values can be determined in a learning phase, during which none or at the most negligible interferences occur with the detection of the ECG signals. In this process, the patient can be located outside the patient tunnel of the magnetic resonance device.

The invention also relates to a device for the electrocardiogram triggering of a measurement of a magnetic resonance device.

The device according to the invention is suited to implementing the described method.

BRIEF DESCRIPTION OF THE DRAWINGS

Further advantages and details of the invention are described on the basis of exemplary embodiments with reference to the figures, in which;

FIG. 5 shows a schematic representation of a fifth exemplary embodiment of the invention and FIG. 6 shows a schematic representation of a sixth exemplary embodiment of the invention.

DETAILED DESCRIPTION OF THE INVENTION

Figure 1:
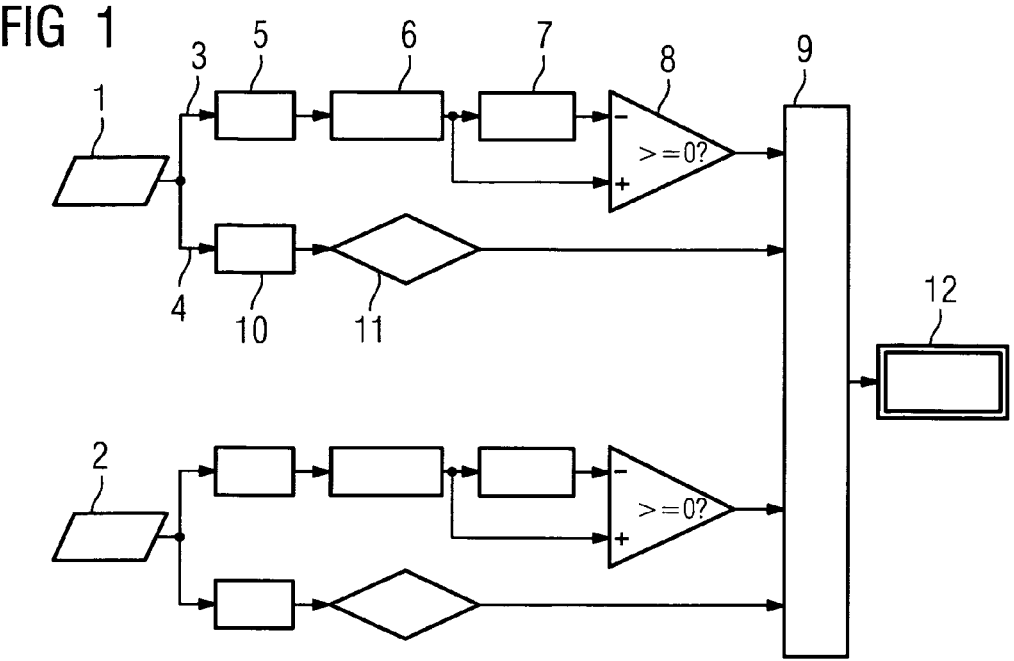
FIG. 1 shows a schematic representation of a first exemplary embodiment of the invention.

As shown in FIG. 1, electrocardiogram signals are received via ECG channels 1, 2 as input data. It is possible for electrocardiogram signals (ECG signals) to also be received by way of further channels (not shown). In either case, at least the two ECG channels 1, 2 shown in FIG. 1 are however used, via which the ECG signals are received.

Prior to the actual magnetic resonance measurement, an initial learning phase is carried out, in which the patient is located outside the patient tunnel of the magnetic resonance device. As a result, this ensures that the signal detection is not interrupted by magnetic or electrical fields in the interior of the patient tunnel. In the learning phase, specific boundary values (threshold values) are determined for the R-wave of the ECG signal. The lower and upper limit values define an interval, which determines the admissible value range for the R-wave.

As shown in FIG. 1, the ECG signals of the ECG channel 1 are further processed in a first branch 3 and in a second branch 4. In the first branch 3, the ECG signals are fed to a low pass filter 5, which is adjusted to MR-specific interferences, the signals are then fed to a derived value sum generator 6, which forms the first or second mathematical derivative or a suitable combination thereof. A threshold value is determined in the threshold value creator 7 by means of an interpolator, said threshold value being compared with the output value of the derived value generator 6 in a comparator 8. The maximum and minimum of the derivation are determined in this way. The maximum and minimum are the limit values for the interval of the admissible values. The maximum of the derived value and/or the derived sum value delimits the R-wave by comparison with the steeper-edged gradient interferences. The lower limit value allows faulty triggering on the less steep-edged T-waves of the heart cycle to be ruled out. The output signal of the comparator 8 is a first comparison result, which is fed to a weighted logic circuit 9.

In the second branch 4, signal processing is carried out in parallel to the first branch 3, in this process the ECG signals are fed to a derived value sum generator 10, which provides the derivation or the sum of the derivation of the ECG signal. In the next step 11, a check is carried out to determine whether the value provided by the derived value sum generator 10 lies between a lower and an upper threshold value, so that a second comparison result is achieved. If the result of this comparison is "yes", in other words when the value 10 supplied by the derived value generator lies between the lower and the upper threshold value, the second comparison result amounts to "yes", which is fed to the weighted logic 9.

The signal processing, which was described for the ECG channel 1, is carried out in an identical fashion for the ECG channel 2, if necessary further ECG channels which are present are also subjected to such signal processing. All comparison results are fed to the weighted logic circuit 9, the triggering 12 of the magnetic resonance device being carried out as a function of the result of the weighted logic circuit 9. The signal processing of the individual channels is carried out here in parallel and essentially simultaneously.

Figure 2:
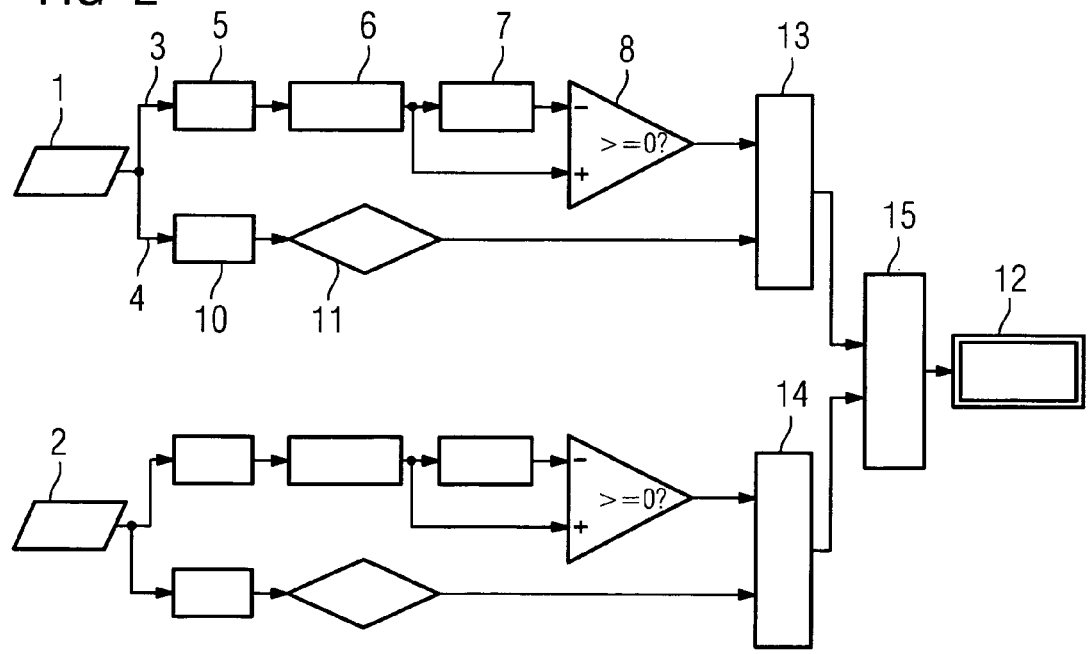
FIG. 2 shows a schematic representation of a second exemplary embodiment of the invention.

FIG. 2 shows a second exemplary embodiment of the invention. Also with this exemplary embodiment, the ECG signals of each channel are processed in two separate branches. In accordance with the first exemplary embodiment, a lowpass filter 5, a derived value generator 6 and a threshold value creator 7 and a comparator 8 are run through in the first branch. A derived value sum generator 10 is run through in the second branch, a check is carried out in step 11 as to whether the value supplied by the derived value sum generator 10 lies within an interval. Unlike in the first exemplary embodiment, the first result supplied by the first branch and the second comparison result supplied by the second branch are linked to one another in a weighted logic circuit 13.

The same applies to the second ECG channel 2, the results of which are linked to one another in a weighed logic circuit 14. The results of the weighted logic circuits 13, 14 are fed to a weighted logic circuit 15, the triggering 12 of the magnetic resonance device being carried out as a function of the result thereof.

Figure 3:
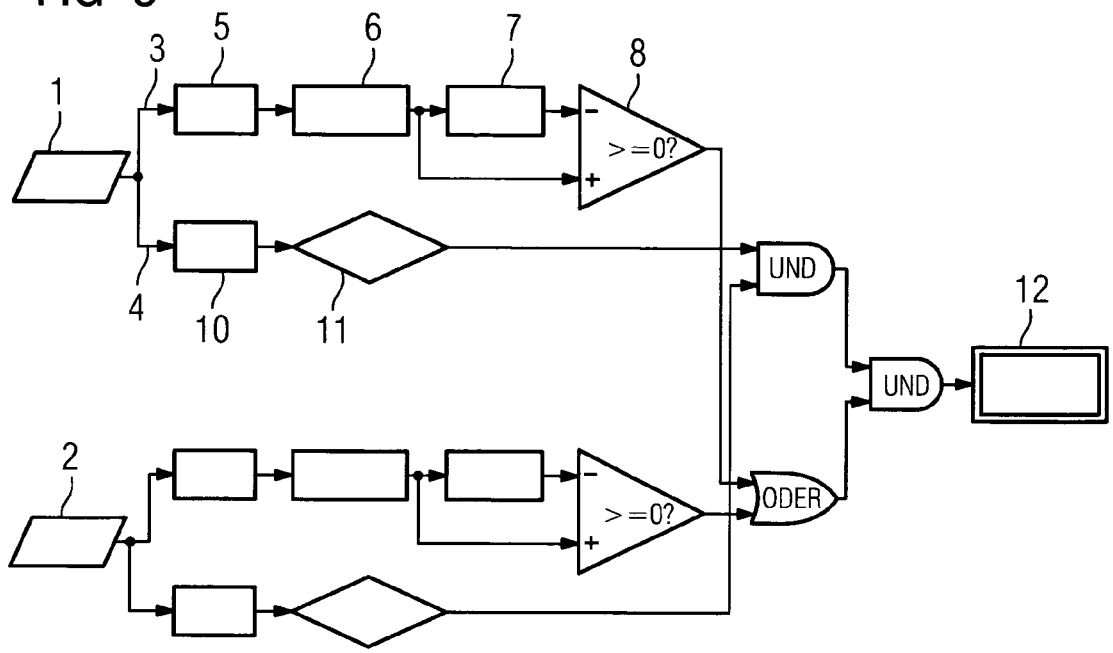
FIG. 3 shows a schematic representation of a third exemplary embodiment of the invention.

FIG. 3 shows a third exemplary embodiment of the invention, using the same reference characters for those components, which correspond to those of the preceding exemplary embodiments. Unlike in the preceding exemplary embodiments, all first comparison results, which are supplied in each instance by the first branch of an ECG channel, are linked to one another in a weighted logic circuit 16. In the exemplary embodiment shown, the logic circuit 16 is an OR link. Similarly, all second comparison results are all second branches of all ECG channels are linked to one another in a weighted logic circuit 17. In the exemplary embodiment illustrated, the logic circuit 17 is an AND circuit. In this process, as shown in FIG. 3, two ECG channels 1, 2 can be used, however the use of a larger number of ECG channels is also possible. The result of the logical link carried out in the logic circuits 16, 16 is fed to a weighed logic circuit 18, which, in the exemplary embodiment illustrated, is embodied as an AND circuit. The triggering 12 is activated as a function of the result of the logic circuit.

Figure 4:
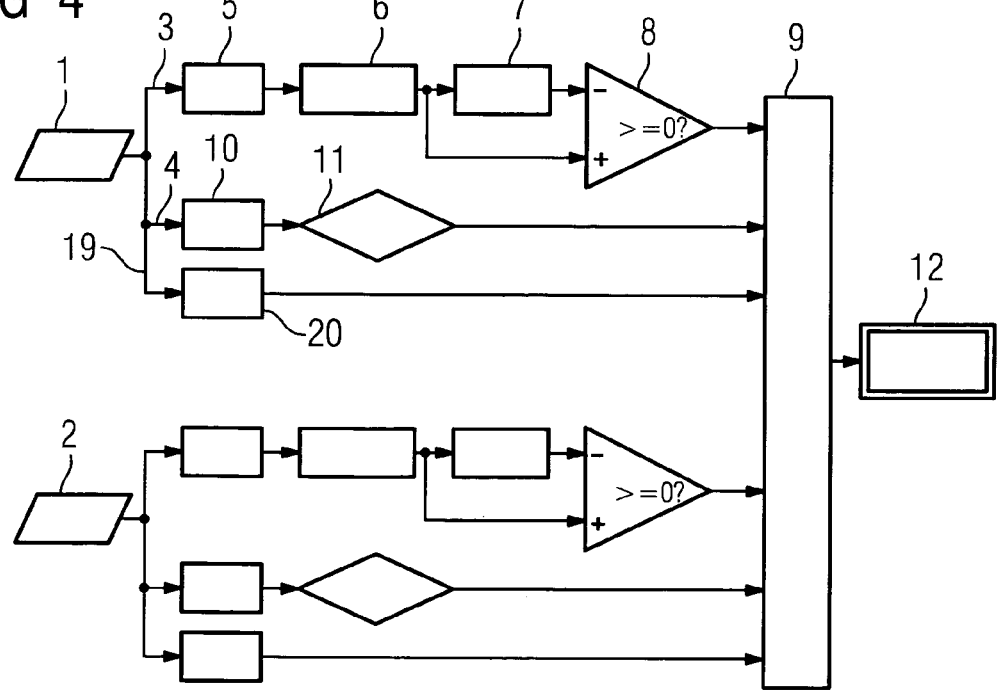
FIG. 4 shows a schematic representation of a fourth exemplary embodiment of the invention.

FIG. 4 shows a fourth exemplary embodiment of the invention. In contrast to the first exemplary embodiment, a third branch 19 is present, in which a signal processing is carried out. The individual branches 3, 4, 19 are executed in parallel, the branch 19 supplies a third comparison result, which is fed to the weighted logic circuit 9 like the first and second comparison results of branches 3, 4, the triggering being activated as a function of the result thereof.

FIG. 5 shows a fifth exemplary embodiment of the invention. As in the fourth exemplary embodiment, a third branch 19 is present, in which a signal processing 20 is carried out. The first, second and third comparison result of branches 3, 4 19 are fed to a weighted logic circuit 21, the lower part of FIG. 5 shows that the same is carried out for the second channel 2, the individual comparison results are fed here to a weighed logic circuit 22. The results of the logical links of the weighted logic circuits 21 and 22 are fed to a weighted logic circuit 23, the triggering 12 being activated as a function of the result thereof.

FIG. 6 shows a sixth exemplary embodiment of the invention. Comparison results a first formed in the branches 3, 4 19 for the channels 1, 2, like the preceding exemplary embodiment. The first comparison results of all channels 1, 2 are fed to a weighted logic circuit 24, similarly all second comparison results are fed to a weighted logic circuit 25, all results of the signal processing 20 carried out in the third branches are fed to a weighted logic circuit 26 and are evaluated in each instance. The results of the weighted logic circuits 24, 25, 26 are fed to a weighted logic circuit 27, the triggering 12 being carried out as a function of the result thereof.

Reference is made here to the fact that the invention also includes all possible combinations of the features described in the individual exemplary embodiments, even if no specific reference is made hereto. The term "signal processing" is generally used in this application for a method for pattern recognition or the application of fuzzy logics and/or a combination of filtering and threshold value formation.

The invention claimed is:

1. A method for triggering a measurement of a magnetic resonance device, comprising:

detecting a first electrocardiogram signal and a second electrocardiogram signal of a patient via a first channel and a second channel of an ECG respectively;
processing the first electrocardiogram signal in a first processing branch of a triggering device by:
    feeding the first electrocardiogram signal to a low pass filter,
    feeding the filtered signal to a first derived value sum generator of the triggering device for generating a first output signal, and
    comparing the first output signal in a first comparator of the triggering device with a threshold value supplied by a threshold value creator for generating a first comparison result of the first electrocardiogram signal;
processing the first electrocardiogram signal in a second processing branch of the triggering device by:
    feeding the first electrocardiogram signal to a second derived value sum generator of the triggering device for generating a second output signal, and
    comparing the second output signal in a second comparator of the triggering device with an upper and a lower threshold value for generating a second comparison result of the first electrocardiogram signal;
repeatly processing the second electrocardiogram signal in the first processing branch and the second processing branch of the triggering device for generating a first and a second comparison results of the second electrocardiogram signal;
evaluating the first and the second comparison results of the first electrocardiogram signal and the first and the second comparison results of the second electrocardiogram signal in a weighted logic circuit; and
triggering the measurement of the magnetic resonance device by the triggering device based on the evaluation, wherein the threshold value is determined in a learning phase during which none or a negligible interference occur with the detection of the electrocardiograph signals.

2. The method as claimed in claim 1, wherein the measurement is cyclically activated by triggering the magnetic resonance device at a trigger point in time.

3. The method as claimed in claim 1, wherein the measurement is started after an adjustable opening time and terminated after an adjustable closing time at a trigger point in time.

4. The method as claimed in claim 1, wherein the measurement is carried out untriggered and a plurality of time stamps are added to data of the measurement as a function of the first and the second electrocardiogram signals.

5. The method as claimed in claim 4, wherein the data of the measurement is subsequently correlated with the first and the second electrocardiogram signals and interpolated.

6. The method as claimed in claim 1, wherein the first and the second derived value sum generators generate a sum of a first or a second mathematical derivation of the first and the second electrocardiogram signals or a combination thereof.

7. The method as claimed in claim 1, wherein the first and the second derived value sum generators generate a mathematical derivation of the first and the second electrocardiograph signals or a sum thereof.

8. The method as claimed in claim 1, wherein the first and the second electrocardiograph signals are processed simultaneously.

9. The method as claimed in claim 1, wherein the first and the second comparison results of the first electrocardiograph signal are evaluated in a first weighted logic circuit and the first and the second comparison results of the second electrocardiograph signal are evaluated in a second weighted logic circuit and the evaluations of the first and the second weighted logic circuits are fed to a further weighted logic circuit.

10. The method as claimed in claim 1, wherein the first comparison results of the first and the second electrocardiograph signals are evaluated in a first weighted logic circuit and the second comparison results of the first and the second electrocardiograph signals are evaluated in a second weighted logic circuit and the evaluations of the first and the second weighted logic circuits are fed to a further weighted logic circuit.

11. The method as claimed in claim 1, wherein the first or the second electrocardiograph signal is processed in a further processing branch for generating a further comparison result and the further comparison result is fed to the weighted logic circuit.

12. The method as claimed in claim 11, wherein the further comparison result is evaluated in a further weighted logic circuit before feeding to the weighted logic circuits.

13. The method as claimed in claim 1, wherein the first and the second electrocardiograph signals are processed based on a method selected from the group consisting of: pattern recognition, fuzzy logic application, and combination of filtering and threshold value formation.

14. The method as claimed in claim 1, wherein the weighted logic circuit amplifies or restricts an influence of a specific electrocardiogram signal during the measurement.

15. The method as claimed in claim 1,
wherein a further electrocardiogram signal of the patient is detected via a further channel,
wherein the further electrocardiogram signal is repeatly processed in the first and the second processing branches for generating a first and a second comparison results of the further electrocardiogram signal, and
wherein the first and the second comparison results of the further electrocardiogram signal are fed to the weighted logic circuit.

* * * * *